US012702468B2

(12) United States Patent
Moda et al.

(10) Patent No.: US 12,702,468 B2
(45) Date of Patent: Aug. 11, 2026

(54) ELECTRODE ASSEMBLY INCLUDING PLATED EMITTERS

(71) Applicant: Stryker Corporation, Kalamazoo, MI (US)

(72) Inventors: Sunil Udaya-Simha Moda, Portage, MI (US); Christopher Scott Brockman, Kalamazoo, MI (US); Brett R. Merkel, Portage, MI (US)

(73) Assignee: Stryker Corporation, Portage, MI (US)

( * ) Notice: Subject to any disclaimer, the term of this patent is extended or adjusted under 35 U.S.C. 154(b) by 857 days.

(21) Appl. No.: 17/914,097

(22) PCT Filed: Mar. 23, 2021

(86) PCT No.: PCT/US2021/023697

§ 371 (c)(1),
(2) Date: Sep. 23, 2022

(87) PCT Pub. No.: WO2021/195091

PCT Pub. Date: Sep. 30, 2021

(65) Prior Publication Data

US 2023/0117847 A1 Apr. 20, 2023

Related U.S. Application Data

(60) Provisional application No. 62/993,317, filed on Mar. 23, 2020.

(51) Int. Cl.

| | |
|---|---|
| ***A61B 18/14*** | (2006.01) |
| ***A61B 90/00*** | (2016.01) |
| *A61B 18/00* | (2006.01) |

(52) U.S. Cl.

CPC .............. *A61B 18/14* (2013.01); *A61B 90/39* (2016.02); *A61B 2018/00077* (2013.01);

(Continued)

(58) Field of Classification Search

CPC .......... A61B 18/14; A61B 2018/00077; A61B 2018/00577; A61B 2018/00821;

(Continued)

(56) References Cited

U.S. PATENT DOCUMENTS

| | | | |
|---|---|---|---|
| 4,267,454 | A | 5/1981 | Playfoot et al. |
| 4,411,266 | A | 10/1983 | Cosman |

(Continued)

FOREIGN PATENT DOCUMENTS

| | | | |
|---|---|---|---|
| CN | 102892453 | A | 1/2013 |
| CN | 104640513 | A | 5/2015 |

(Continued)

OTHER PUBLICATIONS

English language abstract and machine-assisted English translation for JP 2011-505193 A extracted from the PAJ database on Oct. 18, 2024, 38 pages.

(Continued)

*Primary Examiner* — Tigist S Demie

(74) *Attorney, Agent, or Firm* — Howard & Howard Attorneys PLLC

(57) ABSTRACT

An electrode assembly including an elongate body, a proximal emitter, and a distal emitter. A discharge port may be in fluid communication with a lumen of the elongate body. The proximal and distal emitters are formed by plating a metal an outer surface of the elongate body that is polymeric. A portion of the elongate body forms an insulative spacer between the proximal and distal emitters. A distal cap may be coupled to the elongate body, formed from conductive material, and arranged in electrical communication with the distal emitter. A distal lead, a thermocouple, and/or a hypotube may be disposed within the lumen to form an electrical pathway with the distal cap. A sheath may be disposed over a portion of the proximal emitter, and a radiopaque marker (Continued)

may be coupled to the proximal emitter. Methods of fabricating the electrode assembly are also disclosed.

20 Claims, 5 Drawing Sheets

(52) U.S. Cl.
CPC ............... *A61B 2018/00577* (2013.01); *A61B 2018/1465* (2013.01); *A61B 2090/3966* (2016.02)

(58) Field of Classification Search
CPC .... A61B 2018/1465; A61B 2018/1467; A61B 2090/3966; A61B 2217/007; A61B 90/39
See application file for complete search history.

(56) References Cited

U.S. PATENT DOCUMENTS

| | | | | |
|---|---|---|---|---|
| 4,592,372 | A | 6/1986 | Beranek | |
| 5,322,505 | A | 6/1994 | Krause et al. | |
| 5,348,554 | A | 9/1994 | Imran et al. | |
| 5,417,208 | A | 5/1995 | Winkler | |
| 5,545,161 | A | 8/1996 | Imran | |
| 5,782,760 | A | 7/1998 | Schaer | |
| 5,913,854 | A | 6/1999 | Maguire et al. | |
| 6,006,123 | A | 12/1999 | Nguyen et al. | |
| 6,332,881 | B1 | 12/2001 | Carner et al. | |
| 6,447,505 | B2 | 9/2002 | McGovern et al. | |
| 6,669,692 | B1 | 12/2003 | Nelson et al. | |
| 6,679,906 | B2 | 1/2004 | Hammack et al. | |
| 6,706,039 | B2 | 3/2004 | Mulier et al. | |
| 6,740,084 | B2 | 5/2004 | Ryan | |
| 6,878,147 | B2 | 4/2005 | Prakash et al. | |
| 6,882,879 | B2 | 4/2005 | Rock | |
| 6,939,350 | B2 | 9/2005 | Phan | |
| 7,186,234 | B2 | 3/2007 | Dahla et al. | |
| 7,344,533 | B2 | 3/2008 | Pearson et al. | |
| 8,048,070 | B2 | 11/2011 | O'Brien et al. | |
| 8,287,533 | B2 | 10/2012 | Wittkampf et al. | |
| 8,734,440 | B2 | 5/2014 | Wu | |
| 8,758,349 | B2 | 6/2014 | Germain et al. | |
| 8,805,466 | B2 | 8/2014 | Salahieh et al. | |
| 8,894,642 | B2 | 11/2014 | Gibson et al. | |
| 9,370,329 | B2 | 6/2016 | Tun et al. | |
| 9,549,777 | B2 | 1/2017 | Wang et al. | |
| 9,839,443 | B2 | 12/2017 | Brockman et al. | |
| 10,517,611 | B2 | 12/2019 | Patel et al. | |
| 10,912,475 | B2 | 2/2021 | Aujla | |
| 11,160,563 | B2 | 11/2021 | Patel et al. | |
| 11,234,764 | B1 | 2/2022 | Patel et al. | |
| 12,102,436 | B2 | 10/2024 | Stewart et al. | |
| 2002/0026183 | A1 | 2/2002 | Simpson | |
| 2002/0183758 | A1 | 12/2002 | Middleton et al. | |
| 2003/0181901 | A1 | 9/2003 | Maguire et al. | |
| 2005/0107779 | A1 | 5/2005 | Ellman et al. | |
| 2008/0243214 | A1* | 10/2008 | Koblish | A61N 1/05 606/41 |
| 2008/0249595 | A1 | 10/2008 | McDaniel | |
| 2012/0035605 | A1* | 2/2012 | Tegg | A61B 34/73 606/41 |
| 2012/0172857 | A1 | 7/2012 | Harrison et al. | |
| 2012/0310140 | A1 | 12/2012 | Kramer et al. | |
| 2014/0228838 | A1* | 8/2014 | Kirschenman | A61N 1/056 606/41 |
| 2016/0143689 | A1* | 5/2016 | Ditter | A61B 18/1492 606/46 |
| 2017/0348049 | A1 | 12/2017 | Vrba et al. | |
| 2020/0028919 | A1 | 1/2020 | Yang et al. | |
| 2022/0015775 | A1 | 1/2022 | Patel et al. | |

FOREIGN PATENT DOCUMENTS

| | | | |
|---|---|---|---|
| CN | 104684499 | A | 6/2015 |
| CN | 110114026 | A | 8/2019 |
| EP | 3178430 | A1 | 6/2017 |
| JP | 2005144142 | A | 6/2005 |
| JP | 2007509693 | A | 4/2007 |
| JP | 2007537838 | A | 12/2007 |
| JP | 2011505193 | A | 2/2011 |
| WO | 2013163322 | A1 | 10/2013 |
| WO | 2018127796 | A1 | 7/2018 |
| WO | 2018200254 | A2 | 11/2018 |
| WO | 2020198150 | A2 | 10/2020 |

OTHER PUBLICATIONS

International Search Report for Application No. PCT/US2021/023697 dated Jun. 28, 2021, 3 pages.

English language abstract for CN 102892453 A extracted from espacenet.com database on Mar. 26, 2025, 2 pages.

English language abstract for CN 104640513 A extracted from espacenet.com database on Mar. 26, 2025, 1 page.

* cited by examiner 22
40
22
38
44

20
22
38
22
44
40
22
12
46
62
76
72
70
35
34
5
5
78

20
22
34
35
38
40
42
44
46
48
62
70
72
76
78
80
82
84
86
88
90
92
94
96
98
100
104

ELECTRODE ASSEMBLY INCLUDING PLATED EMITTERS

PRIORITY CLAIM

This is a national entry of International Application No. PCT/US2021/023697, filed Mar. 23, 2021, which claims priority to and all the benefits of U.S. Provisional Patent Application No. 62/993,317, filed on Mar. 23, 2020, the entire contents of each being hereby incorporated by reference.

BACKGROUND

An ablation system is often used to selectively destroy nerve tissue to no longer transmit pain signals to the brain. For example, an electrode assembly of the ablation system directs energy to the tissue to heat and destroy the cells of the tissue. Another example includes ablating tumors of the liver, kidney, lung, and bone. Some ablation systems utilize a fluid to improve the delivery of energy across an interface between the electrode assembly and the tissue.

When the pathology is intraosseous, for example, a bone tumor, an introducer assembly may facilitate positioning the electrode assembly at a target location within the bone. In certain instances, it may be desirable for the introducer assembly to provide a curve to access the bone tumor in difficult anatomical locations. One example includes a tumor positioned posteriorly within a vertebral body of the spine. Many known electrode assemblies, particularly those with irrigation capabilities requiring one or more lumens therein, are incapable of flexing sufficiently follow the curve of the introducer assembly without compromise to its function. Moreover, the construction of many known electrode assemblies is intricate and thus associated with increased cost of manufacturing and assembly and increased potential risk of component failure. Therefore, there is a need in the art for an electrode assembly for an ablation system that overcomes one or more of the aforementioned disadvantages.

SUMMARY

The electrode assembly of the present disclosure facilitates the treatment of tissue in anatomical locations not readily accessible with conventional devices. More particularly, the flexibility of the elongate body of the electrode assembly may provide access to the anatomical locations that require greater degrees of curvature and/or sharper radii of curvature, and further may provide infusion fluid to the anatomical locations. The electrode assembly includes an elongate body, a distal emitter, and a proximal emitter that is electrically insulated from the distal emitter such that the electrode assembly is bipolar in construction. The elongate body may be unitary in construction and formed from a flexible material. The elongate body may include continuous portions proximal to proximal emitter, between the distal and proximal emitters, and distal to the distal emitter. The elongate body includes an outer surface, and may further include at least one inner surface defining at least one lumen. In certain implementations, the elongate body is polymeric, in other words, at least partially formed from a polymer. The elongate body may be a tube extruded from polyether ether ketone (PEEK). A first lumen may be configured to direct the infusion fluid from a fluid source to a discharge port. The discharge port may be defined by or disposed on the proximal emitter, or by the portion of the elongate body forming the insulative spacer. The lumen(s) may be optional, and the elongate body may be solid in cross section. The first lumen may be in fluid communication with the discharge port. The first lumen may extend longitudinally pass the discharge port to near the distal end of the elongate body. The distal end of the elongate body may be formed as closed-ended or plugged with a distal cap.

The distal and proximal emitters are coupled to or disposed on elongate body. The distal and proximal emitters may be formed by plating an electrically conductive material to the outer surface of the elongate body that is polymeric. The distal emitter may be formed from plating the metal on a first portion of the outer surface, and the proximal emitter may be formed from plating the metal or another metal on a second portion of the outer surface. The first and second portions may be axially spaced apart from one another such that a portion of the elongate body forms an insulative spacer between the proximal and distal emitters. The distal and proximal emitters are in electrical communication with the conductor so as to be detachably coupled with the energy source. The electrode assembly includes a first electrical pathway in electrical communication with the distal emitter. A thermocouple may be arranged to measure a temperature near the distal end of the electrode assembly. The elongate body may define a second lumen fluidly separate from the first lumen with the first electrical pathway and/or the thermocouple disposed within the second lumen. The first electrical pathway may be a distal lead, or metal plated on the inner surface defining the second lumen. The thermocouple may be secured to the elongate body at or near the distal end.

The distal cap may be coupled to the elongate body, and further may be secured to the elongate body in a manner to seal the lumen(s). The distal cap may be formed from conductive material and arranged in electrical communication with the distal emitter. The distal cap may form a portion of the first electrical pathway to transmit radiofrequency (RF) energy to the distal emitter. The distal cap may be formed from a soldered metal and therefore conductive, or an electrically conductive adhesive may be applied at an interface between the distal cap and the elongate body with the distal cap formed from a metal.

The distal emitter may be disposed on the distal end of the elongate body. A first portion of the distal emitter may be plated on the outer surface of the elongate body, and a second portion of the distal emitter is plated on a surface forming the distal end of the elongate body. The second portion is in electrical communication with the first portion. A proximal surface of the distal cap is secured in a manner to be in electrical communication with the second portion of the distal emitter. The securing of the distal cap may be performed to not only occlude the first lumen and the second lumen, but also to secure leads of the thermocouple in an appropriate position. The distal cap is formed from an electrically conductive material, and further may be formed from a material with sufficient thermal conductivity to effectively transfer heat to be sensed by the leads of the thermocouple. The thermocouple may be further configured to transmit the RF energy to the distal emitter via the distal cap. A third portion of the distal emitter may be plated on a portion the inner surface near the distal end of the elongate body. The third portion is in electrical communication with the second portion and with the first portion. The distal cap may be at least partially disposed or recessed within the first lumen to be in electrical communication with the third portion. An entirety of the distal cap may be disposed within the first lumen such that a distal surface of the distal cap is approximately coterminous with the distal end of the elongate body. A lateral surface of the distal cap is secured to the third portion of the distal emitter. The distal cap may include including a proximal cap portion disposed within the lumen. The proximal cap portion may be in electrical communication with the hypotube and the distal emitter to form a portion of the first electrical pathway. The arrangements in which a portion of the distal cap is disposed within the lumen include the lateral surface secured to the third portion 98 of the distal emitter.

The leads of the thermocouple may be disposed within a hypotube. The hypotube may be coaxially disposed within the first lumen. An annular gap between the hypotube and the inner surface of the elongate body may be in fluid communication with the discharge port. The leads of the thermocouple may be fluidly separated from the infusion fluid. The hypotube may include a distal end secured to the distal cap. The distal end of the hypotube may be closed-ended, and complementarily sized and shaped to a portion of the proximal surface of the distal cap. The hypotube may be formed from an electrically conductive material. The hypotube may be in electrical communication with the conductor, and further configured to transmit the RF energy to the distal emitter via the distal cap. A jacket may be formed from non-conductive material may be disposed between the distal end of the hypotube and the distal cap. The jacket may be configured to electrically insulate the hypotube from the distal cap while not limiting thermal conductivity.

The electrode assembly further include a second electrical pathway in electrical communication with the proximal emitter. The second electrical pathway is configured to transmit RF energy to the proximal emitter. The second electrical pathway may be formed by plating a metal on the inner surface defining the first lumen, a lead, or the like. The electrode assembly may include a sheath formed from non-conductive material. The second electrical pathway may extend between the elongate body and the sheath. The sheath may be heat-shrink tubing with the second electrical pathway being defined by a plated conductor or a proximal lead extending from the proximal emitter. The second electrical pathway and the sheath may extend proximally for an entirety of the length of the elongate body or for a portion thereof.

The electrode assembly may include at least one radiopaque marker having sufficient radiodensity to be visualized on the x-ray imaging. The radiopaque marker may be coupled at any suitable location along the elongate body. The radiopaque marker may be a band coupled to the proximal emitter. The radiopaque marker may be positioned distal to the sheath so as to visually bookend the proximal emitter on the x-ray imaging. The radiopaque marker may form a portion of the second electrical pathway. The radiopaque marker coupled to the proximal emitter, or a band securing the proximal lead to the proximal emitter. The distal cap is formed from electrically conductive material, and may be readily visualized on the x-ray imaging to visually bookend the distal emitter on the x-ray imaging.

According to certain aspects of the present disclosure, an improved method of fabricating an electrode assembly is provided. The elongate body may be formed to define at least one lumen. The elongate body may be extruded to form a segment of a polymeric tube such as PEEK. A discharge port may be removed from the elongate body with the discharge port being in fluid communication with the lumen. The proximal emitter and the distal emitter may be plated on the polymeric tube. A first layer of copper or nickel may be adhered the polymeric tube, and a second layer of gold or platinum may be plated on the first layer. The proximal emitter and the distal emitter are spaced apart by a portion of the polymeric tube forming an insulative spacer. The distal emitter is further plated to a distal end of the elongate body, and a distal cap is secured to the distal end of the elongate body to be in electrical communication with the distal emitter. The distal emitter may be further plated to an inner surface of the elongate body that defines the lumen(s), and the distal cap includes a proximal portion disposed within the lumen and secured to the inner surface. The distal cap is conductive, and may be soldered.

The method may include coupling a thermocouple to the distal cap. The thermocouple may be inserted into a hypotube, and the distal end of the hypotube may be crimped onto leads of the thermocouple to form a thermocouple assembly. The thermocouple assembly may be directed through the lumen and secured to the distal cap. A jacket or adhesive may be arranged between the thermocouple and the hypotube with the jacket or adhesive being electrically insulative but thermally conductive. The hypotube may be arranged in electrical communication with a conductor. Alternatively, a distal lead may be secured to the distal cap. The distal cap may be formed with a relatively small area of solder for the distal lead, after which the distal cap itself is capped with a non-conductive adhesive.

The method may further include arranging a proximal lead in electrical communication with the proximal emitter. The proximal lead may be formed from plating the metal on the elongate body, or a discrete proximal conductor such as a wire. A sheath may be disposed over the electrical pathway, and optionally over a portion of the proximal emitter. The sheath may be tubing that is heat shrunk over the portion of the proximal emitter. A radiopaque marker may be coupled to the proximal emitter. The radiopaque marker may be positioned adjacent the sheath. The radiopaque marker may be a band crimped or swaged onto the proximal lead. The distal cap is formed from a conductive material, and with the radiopaque marker provide visual indicia on x-ray imaging that bookend the distal and proximal emitters, respectively. The electrode assembly may be arranged in a kit with an access cannula and an introducer device. The result is a lower cost, potentially disposable electrode assembly that provides infusion with improved flexibility to access anatomical locations with greater degrees of curvature and/or sharper radii of curvature.

BRIEF DESCRIPTION OF THE DRAWINGS

Advantages of the present invention will be readily appreciated as the same becomes better understood by reference to the following detailed description when considered in connection with the accompanying drawings. It should be appreciated that the drawings are illustrative in nature and are not necessarily drawn to scale.

DETAILED DESCRIPTION

Figures 1, 2:
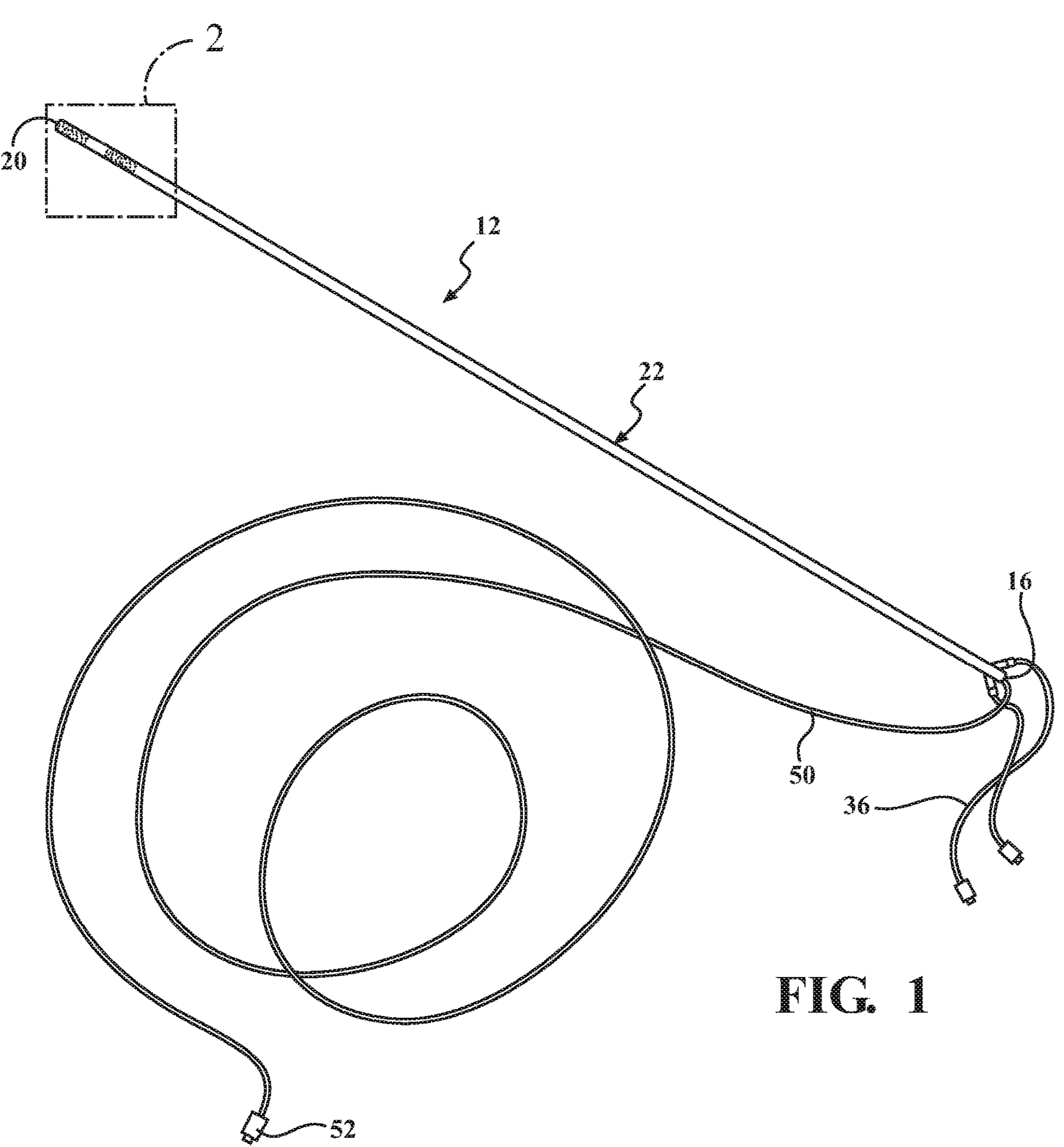
FIG. 1 is a perspective view of an ablation system including an electrode assembly.
FIG. 2 is a detailed view of the electrode assembly of FIG. 1 within detail 2.

Referring to FIG. 1, an ablation system includes an electrode assembly 12 configured to treat tissue. The electrode assembly 12 includes an elongate body 22 having a length defined between a proximal end 16 opposite a distal end 20. Near the distal end 20 of the elongate body 22, the electrode assembly 12 includes a distal emitter 38, and a proximal emitter 40 positioned proximally relative to the distal emitter 38. The distal emitter 38 and the proximal emitter 40 may be electrically insulated from one another such that the electrode assembly 12 is bipolar in construction. Aspects of the present disclosure may be provided on a monopolar electrode assembly requiring a grounding source, for example, a ground pad.

The electrode assembly 12 includes at least one conductor 50 in electrical communication with the distal and proximal emitters 38, 40, and a connector 52 in electrical communication with the conductor 50. The connector 52 is configured to be detachably coupled with an energy source 54, for example, an electrosurgical generator. One suitable energy source 54 is an radiofrequency generator and control console sold under the tradenames MultiGen (MG1) and MultiGen 2 (MG2) by Stryker Corporation (Kalamazoo, Mich.), and those described in commonly-owned International Publication No. WO 2018/0200254, published Nov. 1, 2018, the entire contents of which are hereby incorporated by reference. The energy source 54 may capable of sourcing a variable current to the electrode assembly 12. The control console may allow adjustment of frequency, current, and/or voltage levels of the sourced current for various time periods. Energy from the energy source 54 is delivered to the distal and proximal emitters 38, 40 in a manner such that the distal and proximal emitters 38, 40 have opposite polarity. When positioned within or adjacent tissue, energy passing between the distal and proximal emitters 38, 40 facilitates heating and ablating the tissue, or alternatively, electrosurgical cutting or coagulation.

Figures 3, 4, 5:
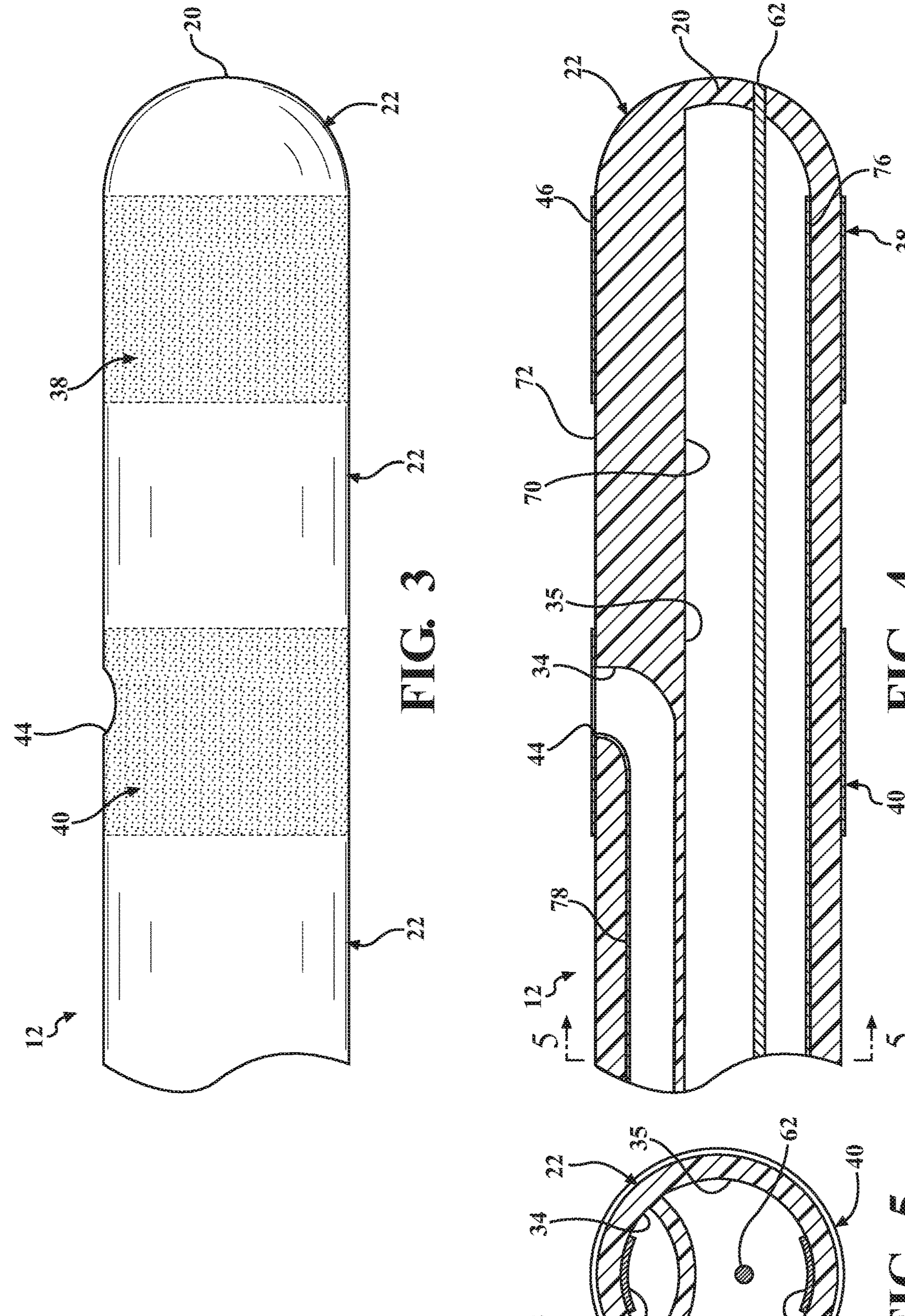
FIG. 3 is an elevation view of a portion of the electrode assembly of FIG. 1.
FIG. 4 is a sectional view of the portion of the electrode assembly of FIG. 3.
FIG. 5 is an axial view of the portion of the electrode assembly of FIG. 3 taken along line 5-5.

As mentioned, conventional electrode assemblies, especially those with fluid infusion, irrigation, or internal cooling, are generally incapable of achieving more than minimal curvature. Those electrode assemblies are unable to achieve sufficient posterior access within a vertebral body through a unipedicular approach, among other procedures requiring off-axis positioning. The electrode assembly 12 of the present disclosure advantageously provides for the elongate body 22 being highly flexible. Further, the elongate body 22 may extend near or to the distal end 20 of the electrode assembly 12 such that nearly an entirety of the length of the elongate body 22 is flexible. In other words, the elongate body 22 may be unitary in construction from a flexible material and extend at least distal to the proximal emitter 40, and in some cases distal to the distal emitter 38. For example, FIG. 3 shows the elongate body 22 having continuous portions proximal to proximal emitter 40, between the distal and proximal emitters 38, 40, and distal to the distal emitter 38. In alternative implementations, it is contemplated that the elongate body 22 be formed from more than one subcomponent. Based on its flexibility, the elongate body 22 is configured to bend or curve when deployed through an introducer assembly 13 (see FIG. 11) in a manner to be further described.

The elongate body 22 may define the distal end 20 of the electrode assembly 12, and the elongate body 22 may define the proximal end 16. In certain implementations, the electrode assembly 12 includes a hub 23 (see FIG. 11) with the elongate body 22 extending distally from the hub 23. Referring now to FIGS. 3 and 4, the elongate body 22 includes an outer surface 72, and may further include at least one inner surface 70 defining at least one lumen 34, 35 to be described. In certain implementations, the elongate body 22 is polymeric, in other words, at least partially formed from a polymer. The elongate body 22 may be extruded, molded, or shaped through other suitable manufacturing techniques, and may be formed from films, fibers, fabrics, and powders. In one example, the elongate body 22 is a tube extruded from polyether ether ketone (PEEK), which is highly flexible and includes material properties well suited for medical devices. Further, in implementations with more than one lumen 34, 35, extruding the PEEK tube may reduce manufacturing complexities and costs over known devices. Other suitable materials are contemplated, for example, polytetrafluoroethylene (Teflon™), phenolic, polycarbonate, polysulfane, and polyoxymethylene, among others. The suitable materials may include a Young's modulus of less than 3.6 gigapascals (GPa).

The distal and proximal emitters 38, 40 are coupled to or disposed on elongate body 22. More particularly, the distal and proximal emitters 38, 40 may be formed by plating an electrically conductive material to the outer surface 72 of the elongate body 22 that is polymeric. An exemplary plating process includes electroplating a metal on the elongate body 22 that is polymeric, which is schematically represented by the stippling in FIGS. 1-3. One suitable manufacturing process for plating a metal on a polymer has been developed by SAT Plating (Troy, Mich.). In one example, the metal is gold, but other suitable metals include copper, nickel, stainless steel, titanium, and chrome, among others. For example, a first layer of copper or nickel may be adhered to the polymeric tube, and a second layer of gold or platinum may be plated on the first layer. The plating of the metal on the polymeric material renders the distal and proximal emitters 38, 40 electrically conductive to transmit the RF energy without adverse effect on the flexibility of the elongate body 22. Other suitable manners by which the proximal and distal emitters may be plated are electroless plating, electrodeposition, immersion, physical vapor deposition (PVD), chemical vapor deposition (CVD), plasma spray, and the like.

As mentioned, the distal emitter 38 is spaced apart and electrically insulated from the proximal emitter 40, as is necessary for the electrode assembly 12 to be operable as a bipolar electrode. The distal emitter 38 may be formed from plating the metal on a first portion 56 of the outer surface 72, and the proximal emitter 40 may be formed from plating the metal or another metal on a second portion 58 of the outer surface 72. The first and second portions 56, 58 may be axially spaced apart from one another such that a portion of the elongate body 22 forms an insulative spacer 42 between the proximal and distal emitters 38, 40. For example, in implementations where the elongate body 22 is a PEEK tube, the PEEK tube itself is non-conductive and therefore forms the insulative spacer 42 between the proximal and distal emitters 38, 40. The proximal and distal emitters 38, 40 are therefore electrically insulated without the need for a discrete insulative spacer that may require mechanical coupling along with adhesives, threading, lap joints, or the like. In addition to increased flexibility and reduced manufacturing complexity and cost as previously described, the arrangement eliminates interfaces between the discrete components and the corresponding possibility of egress of infusion fluid through the interfaces, particularly with bending of the electrode assembly 12 at greater bend angles and sharper curvatures. Egress of fluid at the interfaces may otherwise result in the virtual electrode during operation being "within" a device, which may compromise functionality of the same. The electrode assembly 12 of the present disclosure overcomes this shortcoming.

A first lumen 34 may be configured to direct an infusion fluid from a fluid source (not shown) to a discharge port 44. The discharge port 44 may be positioned at any suitable location along the length of the elongate body 22, and more than one discharge port 44 may be provided. FIGS. 2-4 show the discharge port 44 defined by or disposed on the proximal emitter 40, and FIGS. 5-10 show the discharge portion defined by the portion of the elongate body 22 forming the insulative spacer 42, i.e., between the proximal and distal emitters 38, 40. Having the discharge port 44 positioned proximal to the distal emitter 38 may advantageously provide for the infusion fluid descending along a surface of the distal emitter 38 under the influence of gravity when the electrode assembly 12 is deployed within the anatomy at an angle of approach. For example, micro infusion of the fluid (e.g., saline or another conductive fluid) with a microinfusion module (not shown) facilitates energy transfer across the tissue-emitter interface, which helps control temperature, impedance, hydration, and ion concentration to prevent charring of biological tissue. One suitable microinfusion module disclosed in commonly-owned International Publication No. WO2020/0198150, published Nov. 5, 2020, the entire contents of which are hereby incorporated by reference. The microinfusion module may be releasably coupled to the electrode assembly 12, for example, with a Luer lock fitting coupled to a fluid coupling 36 (see FIG. 1). The microinfusion module may be considered "micro" because of its relatively small form factor, and/or amounts of the fluid may be infused at relatively low rates. However, it should be appreciated that the lumen(s) 34, 35 are optional, and the elongate body 22 may be solid in cross section. The resulting electrode assembly may not provide for infusion, and electronic subcomponents may be arranged along the outer surface 72 of the elongate body 22. One or more sheaths may be provided to electrically insulate certain components as needed.

The first lumen 34 is in fluid communication with the discharge port 44, and otherwise may be arranged in any suitable manner within the elongate body 22. For example, FIG. 4 shows the first lumen 34 extending longitudinally within a portion of the elongate body 22, and further turning radially outward to the discharge port 44. FIGS. 6-10 show the first lumen 34 extending longitudinally pass the discharge port to near the distal end 20 of the elongate body 22. In implementations where the first lumen 34 extends distal to the discharge port 44, the distal end 20 of the elongate body 22 may be formed as closed-ended (FIG. 4) or plugged with a distal cap 46 (FIGS. 6-10) to be described in detail. For example, the distal end 20 of the elongate body 22 shown in FIG. 4 may be formed by a catheter tipping process in which heat is applied to at least partially round, taper, or close the distal end 20 of the elongate body 22. Alternatively, the distal end 20 may define the discharge port 44 or another discharge port. FIGS. 6-10 show the lumen 34, 35 extending to a distal end 84 of the elongate body 22 with the distal cap 46 coupled to the distal end 84 of the elongate body 22. The arrangement may result in the lumen 34, 35 extending an entirety of the length of the elongate body 22 with the elongate body 22 being constant in axial cross section, a form factor particularly well suited for the elongate body 22 being extruded, which itself is a less complex and more cost effective manufacturing process for fabricating smaller devices on the level of 22 gauge, 14 gauge, and the like, as is the case here in certain implementations. Likewise, fabrication of multi-lumen tubing may also be accomplished through extrusion in an efficient manner. Other suitable manufacturing techniques may include vacuum molding, injection molding, blow molding, additive manufacturing, braiding, and the like.

The distal and proximal emitters 38, 40 are in electrical communication with the conductor 50 so as to be detachably coupled with the energy source 54. To facilitate the electrical connection, the electrode assembly 12 includes a first electrical pathway 76 in electrical communication with the distal emitter 38. Further, the electrode assembly 12 may include a thermocouple 62 arranged to measure a temperature near the distal end 20 of the electrode assembly 12, which is schematically shown in FIG. 4 and depicted as a pair of leads 80, 82 FIGS. 6-10. The control console may be configured to regulate the RF energy being delivered based on the temperature measured by the thermocouple 62, along with other measured parameters. The elongate body 22 may define a second lumen 35 fluidly separate from the first lumen 34 with the first electrical pathway 76 and/or the thermocouple 62 disposed within the second lumen 35. With continued reference to FIG. 4, the first electrical pathway 76 may extend through the second lumen 35 to be in electrical communication with the distal emitter 38. For example, the first electrical pathway 76 may be a distal lead 92, or metal plated on the inner surface 70 defining the second lumen 35. A small hole (not shown) may extend from the inner surface 70 to the outer surface 72 to provide the electrical communication between the first electrical pathway 76 within the second lumen 35 and the distal emitter 38 on the outer surface 72. The thermocouple 62 may be secured to the elongate body 22 at or near the distal end 20 with any suitable joining means. In certain implementations, one or more additional thermocouples (not shown) may be positioned proximal to the proximal emitter 40. The additional thermocouple(s) may be configured to monitor progression of the ablated lesion in a more proximal position than the distal end 20 of the electrode assembly 12. The control console may be configured to regulate the RF energy being delivered based on the temperature measured by the additional thermocouple(s).

The multi-lumen arrangement prevents potential compromise of electrical components with the infusion fluid. Further, since the elongate body 22 itself provides the barrier separating the first lumen 34 from the second lumen 35, there is little sacrifice to the flexibility of the elongate body 22 and lesser concern for compromise of internal subcomponents or interfaces between the same.

Referring now to FIGS. 6-10, the distal cap 46 may be coupled to the elongate body 22. The distal cap 46 may define the distal end 20 of the electrode assembly 12. The distal cap 46 may be secured to the elongate body 22 in a manner to seal the lumen 34, 35. Furthermore, the distal cap 46 may be formed from conductive material and arranged in electrical communication with the distal emitter 38. As to be further described, the distal cap 46 may form a portion of the first electrical pathway 76 to transmit RF energy to the distal emitter 38. The distal cap 46 may be arranged in electrical communication with the distal emitter 38 that is positioned on the outer surface 72 of the elongate body 22 with the distal lead 92 (and/or the thermocouple 62) disposed within the lumen 34, 35. In such an arrangement, the electrical subcomponents of the electrode assembly 12 may be internal to the elongate body 22 while still transmitting the necessary RF energy to the distal emitter 38 on an exterior of the elongate body 22. In one example, the distal cap 46 itself is formed from a soldered metal and therefore conductive, and in another example, an electrically conductive adhesive may be applied at an interface between the distal cap 46 and the elongate body 22 with the distal cap 46 formed from a metal. In certain implementations, the distal cap 46 may be formed from a non-thermal and non-electrically conductive material. For example, the distal cap 46 may be formed with a relatively small area of solder for the distal lead 92, after which the distal cap 46 itself is capped with a non-conductive adhesive.

Figures 6, 7, 8:
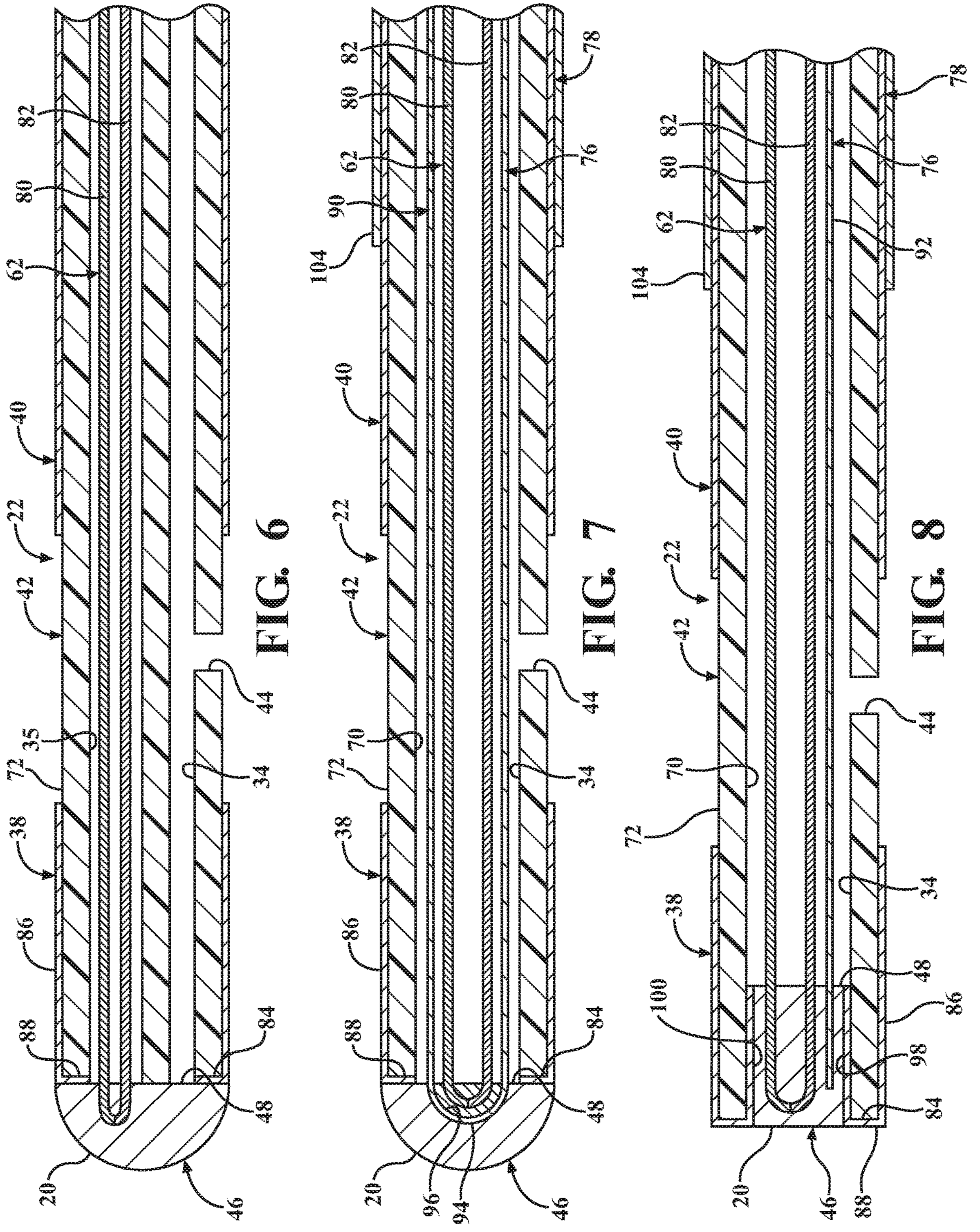
FIG. 6 is a sectional view of a portion of another implementation of the electrode assembly.
FIG. 7 is a sectional view of a portion of another implementation of the electrode assembly.
FIG. 8 is a sectional view of a portion of another implementation of the electrode assembly.

FIG. 6 illustrates an implementation of the electrode assembly 12 in which a portion of the distal emitter 38 is disposed on the distal end 84 of the elongate body 22. More particularly, a first portion 86 of the distal emitter 38 is plated on the outer surface 72 of the elongate body 22, and a second portion 88 of the distal emitter 38 is plated on a surface forming the distal end 84 of the elongate body 22. The second portion 88 is in electrical communication with the first portion 86, and may be considered a lip extending radially inwardly about the distal end 84 of the elongate body 22. A proximal surface 48 of the distal cap 46 is secured in a manner to be in electrical communication with the second portion 88 of the distal emitter 38. The soldered metal itself, upon solidifying, may include the proximal surface 48, or alternatively the distal cap 46 may be a discrete metal component including the proximal surface 48.

The implementation of FIG. 6 further shows the elongate body 22 defining the first lumen 34, and the second lumen 35 fluidly separate from the first lumen 34. The leads 80, 82 of the thermocouple 62 extend through the second lumen 35 and are secured to the distal cap 46. The soldering of the distal cap 46 may be performed to not only occlude the first lumen 34 and the second lumen 35, but also to secure the leads 80, 82 of the thermocouple 62 in an appropriate position. Alternatively, the leads 80, 82 may be secured to the distal cap 46 with adhesive, crimping, friction fit, or the like. The distal cap 46 is formed from an electrically conductive material, and further may be formed from a material with sufficient thermal conductivity. The distal cap 46 effectively transfers heat from the adjacent tissue undergoing ablation, for example, and the heat is sensed by the leads 80, 82 of the thermocouple 62, which itself is electrically conductive. The electrical signals indicative of a temperature are transmitted from the thermocouple 62 to the control console. Moreover, with the leads 80, 82 of the thermocouple 62 being electrically conductive, in certain implementations it is contemplated that the thermocouple 62 may be further configured to transmit the RF energy to the distal emitter 38 via the distal cap 46. In such an arrangement, the first electrical pathway 76 may not require the distal lead 92 for to transmitting the RF energy from the conductor 50 to the distal emitter 38 (see FIGS. 3 and 8).

Referring now to FIG. 7, another implementation of the electrode assembly 12 is shown in which a hypotube 90 is provided, wherein the leads 80, 82 are disposed within the hypotube 90. Whereas FIG. 6 shows the elongate body 22 defining the first and second lumens 34, 35, FIG. 7 shows a singular lumen (the first lumen 34) with the hypotube 90 coaxially disposed within the first lumen 34. In such an arrangement, the first lumen 34, and in particularly an annular gap between the hypotube 90 and the inner surface 70 of the elongate body 22, is in fluid communication with the discharge port 44. The leads 80, 82 of the thermocouple 62 are fluidly separated from the infusion fluid.

The hypotube 90 may include a distal end 94 secured to the distal cap 46, for example, with solder, adhesive, or the like. Further, the first portion 86 of the distal emitter 38 is plated on the outer surface 72 of the elongate body 22, and the second portion 88 of the distal emitter 38 is plated on the surface forming the distal end 84 of the elongate body 22 with the first and second portions 86, 88 in electrical communication with the distal cap 46. The distal end 94 of the hypotube 90 may be closed-ended as shown, and in one example, a portion of the proximal surface 48 of the distal cap 46 is hemispherical with the distal end 94 of the hypotube 90 being hemispherical and complementary in size and shape. The hypotube 90 may be formed from an electrically conductive material, for example, stainless steel. In certain implementations it is contemplated that the hypotube 90 may be in electrical communication with the conductor 50, and further configured to transmit the RF energy to the distal emitter 38 via the distal cap 46. In such an arrangement, the first electrical pathway 76 may not require the distal lead 92 for to transmitting the RF energy to the distal emitter 38 (see FIGS. 3 and 8). It should also be appreciated that the hypotube 90 may be formed with sufficient flexibility so as not to limit the flexibility of the elongate body 22. With the hypotube 90 formed from electrically conductive material, a jacket 96 formed from non-conductive material may be disposed between the distal end 94 of the hypotube 90 and the thermocouple 62. The jacket 96 may be configured to electrically insulate the hypotube 90 from the thermocouple 62 while not limiting thermal conductivity between the same. Examples of material suitable for the jacket 96 may include thermal adhesive or heat-shrink.

FIG. 8 illustrates an implementation of the electrode assembly 12 in which the first portion 86 of the distal emitter 38 is plated on the outer surface 72 of the elongate body 22, the second portion 88 of the distal emitter 38 is plated on the surface forming the distal end 84 of the elongate body 22, and a third portion 98 is plated on a portion the inner surface 70 near the distal end 84 of the elongate body 22. The third portion 98 is in electrical communication with the second portion 88 and with the first portion 86, and the distal emitter 38 may be considered generally cylindrical in form. The illustrated implementation shows the first portion 86 extending proximally from the distal end 84 of the elongate body 22 to a greater distance than the third portion 98, however, alternative relative dimensions are contemplated.

Figure 9:
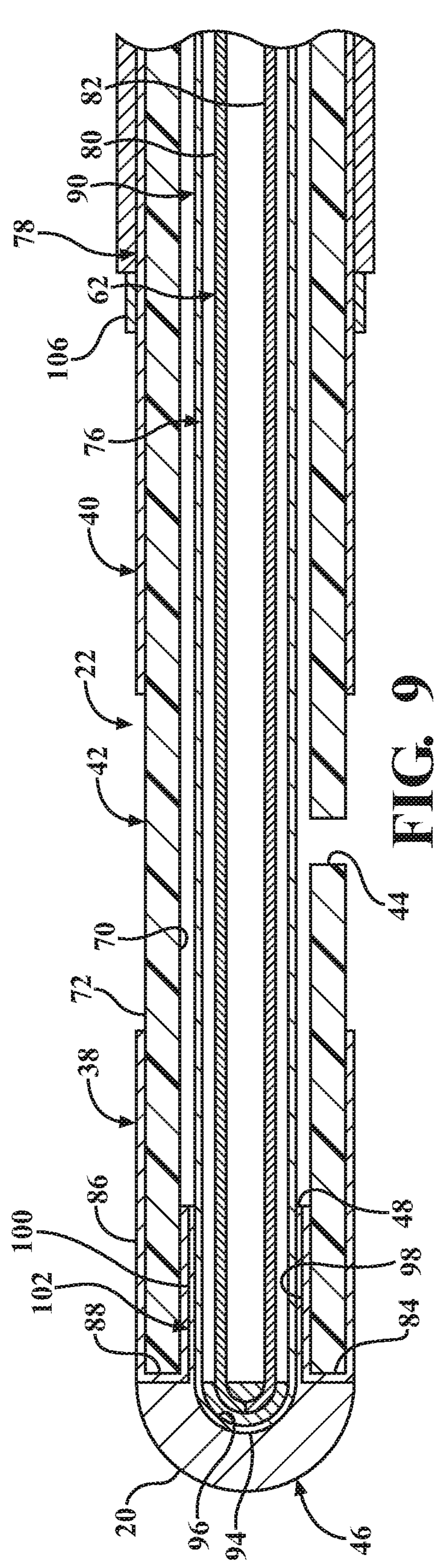
FIG. 9 is a sectional view of a portion of another implementation of the electrode assembly.
Figure 10:
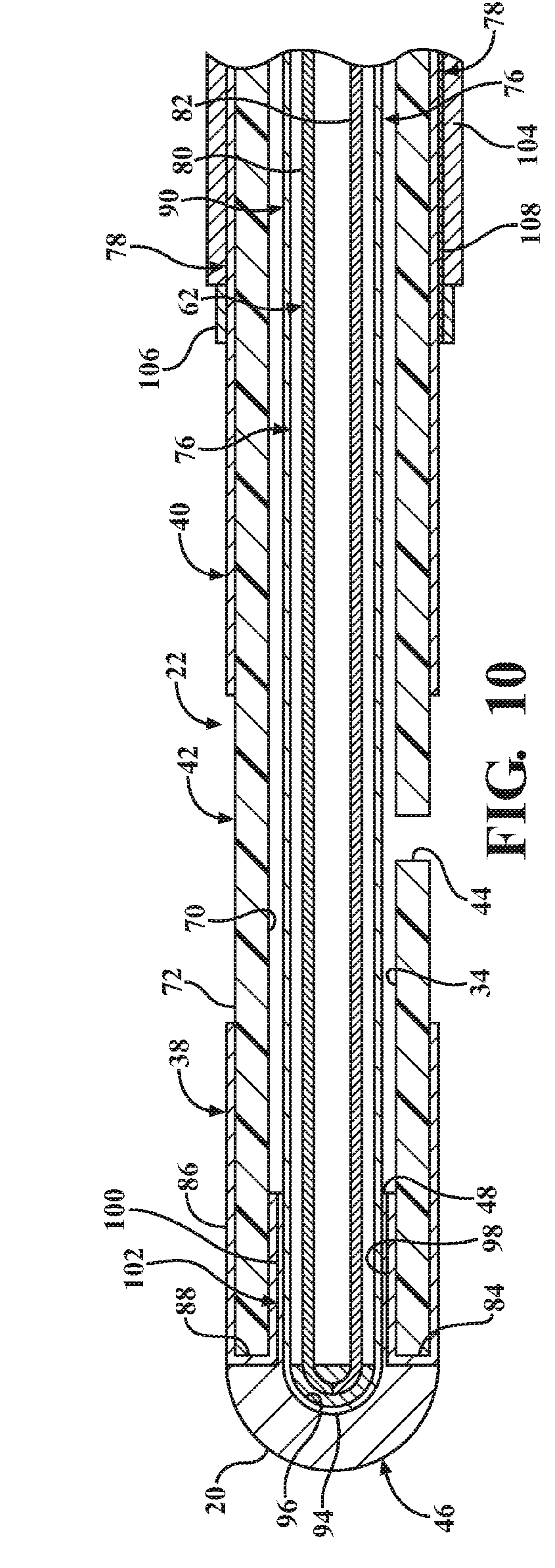
FIG. 10 is a sectional view of a portion of another implementation of the electrode assembly.

With the third portion 98 disposed within the first lumen 34, the distal cap 46 may be at least partially disposed or recessed within the first lumen 34 to be in electrical communication with the third portion 98 (see also FIGS. 9 and 10). FIG. 8 shows an entirety of the distal cap 46 disposed within the first lumen 34 such that a distal surface of the distal cap 46 is approximately coterminous with the distal end 84 of the elongate body 22. A lateral surface 100 of the distal cap 46 is secured to the third portion 98 of the distal emitter 38. The soldered metal itself, upon solidifying, may include the lateral surface 100, or alternatively the distal cap 46 may be a discrete metal component including the lateral surface 100.

The implementation of FIG. 8 further shows the elongate body 22 defining the first lumen 34 with the leads 80, 82 of the thermocouple 62 and the distal lead 92 of the electrical pathway 74 disposed within the first lumen 34. It should be appreciated that the leads 80, 82, 92 may be disposed within a jacket or sheath (not shown) to electrically insulate the electrical components from the infusion fluid. It should be further appreciated that the distal cap 46 of the present implementation may be used in combination with the hypotube 90, the elongate body 22 with the first and second lumens 34, 35, and/or any other compatible implementation of the present disclosure.

FIG. 8 shows the distal cap 46 disposed within the lumen 34, and FIGS. 9 and 10 show the distal cap 46 being dome-shaped and further including a proximal cap portion 102 disposed within the lumen 34. In one implementation, the distal cap 46 may be more easily soldered within the lumen 34 as opposed to reproducibly soldering the dome-shaped end. The proximal cap portion 102 may be in electrical communication with the hypotube 90 and the distal emitter 38 to form a portion of the first electrical pathway 76. The arrangements in which a portion of the distal cap 46 is disposed within the lumen 34 include the lateral surface 100 secured to the third portion 98 of the distal emitter 38. Among other advantages, the interface between the lateral surface 100 and the third portion 98 are subject to shear forces as opposed to tensile forces and provide a more robust design for accommodating fluid under pressure. The infusion fluid may be at a pressure of approximately one (1) bar, but the distal cap 46 may be configured to accommodate greater pressures.

The first electrical pathway 76 is configured to transmit RF energy to the distal emitter 38. The electrode assembly 12 further include a second electrical pathway 78 in electrical communication with the proximal emitter 40 and configured to transmit RF energy to the same. Referring again to FIG. 4, the second electrical pathway 78 traverses the bend defined by the first lumen 34 to be coupled to the proximal emitter 40. The second electrical pathway 78 may be formed by plating a metal on the inner surface 70 defining the first lumen 34, a lead, or the like. The first electrical pathway 76 should be insulated from the second electrical pathway 78 yet extend axially past the proximal emitter 40, and therefore positioning the first electrical pathway 76 within the interior of the elongate body 22 may be desirable. In other words, there may be less concern for arcing or electrical compromise by having the first electrical pathway 76 within the lumen 34, 35 as opposed to, for example, the distal lead 92 lead extending along the outer surface 72 of the elongate body 22 across the proximal emitter 40. Such concerns are less pronounced with the proximal emitter 40, as a lead extending proximally from the proximal emitter 40 does not electrically implicate the distal emitter 38 in any manner. However, it is contemplated that the proximal emitter 40 may be C-shaped to define a gap (not shown) with the distal lead 92 extending through the gap in a manner that is electrically insulated from the proximal emitter 40.

Referring now to FIGS. 7-10, the electrode assembly 12 may include a sheath 104 formed from non-conductive material. The second electrical pathway 78 may extend between the elongate body 22 and the sheath 104. In certain implementations, the sheath 104 is heat-shrink tubing with the second electrical pathway 78 being defined by a plated conductor or a proximal lead 108 extending from the proximal emitter 40. FIGS. 7-9 show the plated conductor that may be considered a portion of the proximal emitter 40 disposed beneath the sheath 104. The plated conductor beneath the sheath 104 may extend about the outer diameter of the elongate body 22 like the proximal emitter 40, or be narrowly shaped akin to a plated lead. FIG. 10 shows the proximal lead 108 being coupled to an outside surface of the proximal emitter 40 and disposed between the sheath 104 and the elongate body 22. The second electrical pathway 78 and the sheath 104 may extend proximally for an entirety of the length of the elongate body 22 or for a portion thereof. In one example, the second electrical pathway 78 and the sheath 104 may extend proximally until being disposed beneath the hub 23 coupled over a proximal portion of the elongate body 22 (see FIG. 11).

Owing to the elongate body 22 being polymeric, the elongate body 22 may be relatively radiolucent on fluoroscopy and other x-ray imaging. The electrode assembly 12 of the present disclosure includes at least one radiopaque marker 106 having sufficient radiodensity to be visualized on the x-ray imaging. The radiopaque marker 106 may be coupled at any suitable location along the elongate body 22. In an exemplary implementation and with reference to FIGS. 9 and 10, the radiopaque marker 106 is a band coupled to the proximal emitter 40. Further, the radiopaque marker 106 may be positioned just distal to the sheath 104 so as to visually bookend the proximal emitter 40 on the x-ray imaging. The radiopaque marker 106 may be formed from a metal such as platinum or platinum iridium to be easily visualized on the x-ray imaging. The radiopaque marker 106 may form a portion of the second electrical pathway 78. For example, FIG. 9 shows the radiopaque marker 106 coupled to the proximal emitter 40, and FIG. 10 shows the radiopaque marker 106 being a band securing the proximal lead 108 to the proximal emitter 40. The radiopaque marker 106 may be crimped, swaged, or otherwise secured to the proximal emitter 40 or the elongate body 22.

As previously described, the distal cap 46 is formed from electrically conductive material. As such, the distal cap 46 may be readily visualized on the x-ray imaging to visually bookend the distal emitter 38 on the x-ray imaging. With the elongate body 22 may be relatively radiolucent, the distal cap 46 and the radiopaque marker 106 may be especially pronounced on the x-ray imaging to facilitate accurate positioning within an anatomical location of interest. It is readily appreciated that the distal cap 46, therefore, provides several functions associated with the electrode assembly 12. In certain implementation, another radiopaque marker (not shown) may be a band that is swaged near the distal end 20 of the electrode assembly 12. Such an arrangement may be particularly well suited for instances where the distal cap 46 is an adhesive or formed from another material that is not sufficiently radiopaque. Additionally or alternatively, the proximal and distal emitters 38, 40 formed from plating the metal may be themselves radiopaque. For example, plating with a sufficiently thick layer of a metal having a high atomic weight such as gold of platinum may provide sufficient radiodensity to be visualized on the x-ray imaging. It is still further contemplated that the radiopaque marker(s) 106 need not be disposed on or coupled to the outer surface 72 of the elongate body 22. In certain implementations, the radiopaque marker(s) 106 may be disposed within the lumen 34, 35. For example, segments of wire, such as tungsten wire, may be secured at one or more desired positions within the lumen 34, 35.

Figure 11:
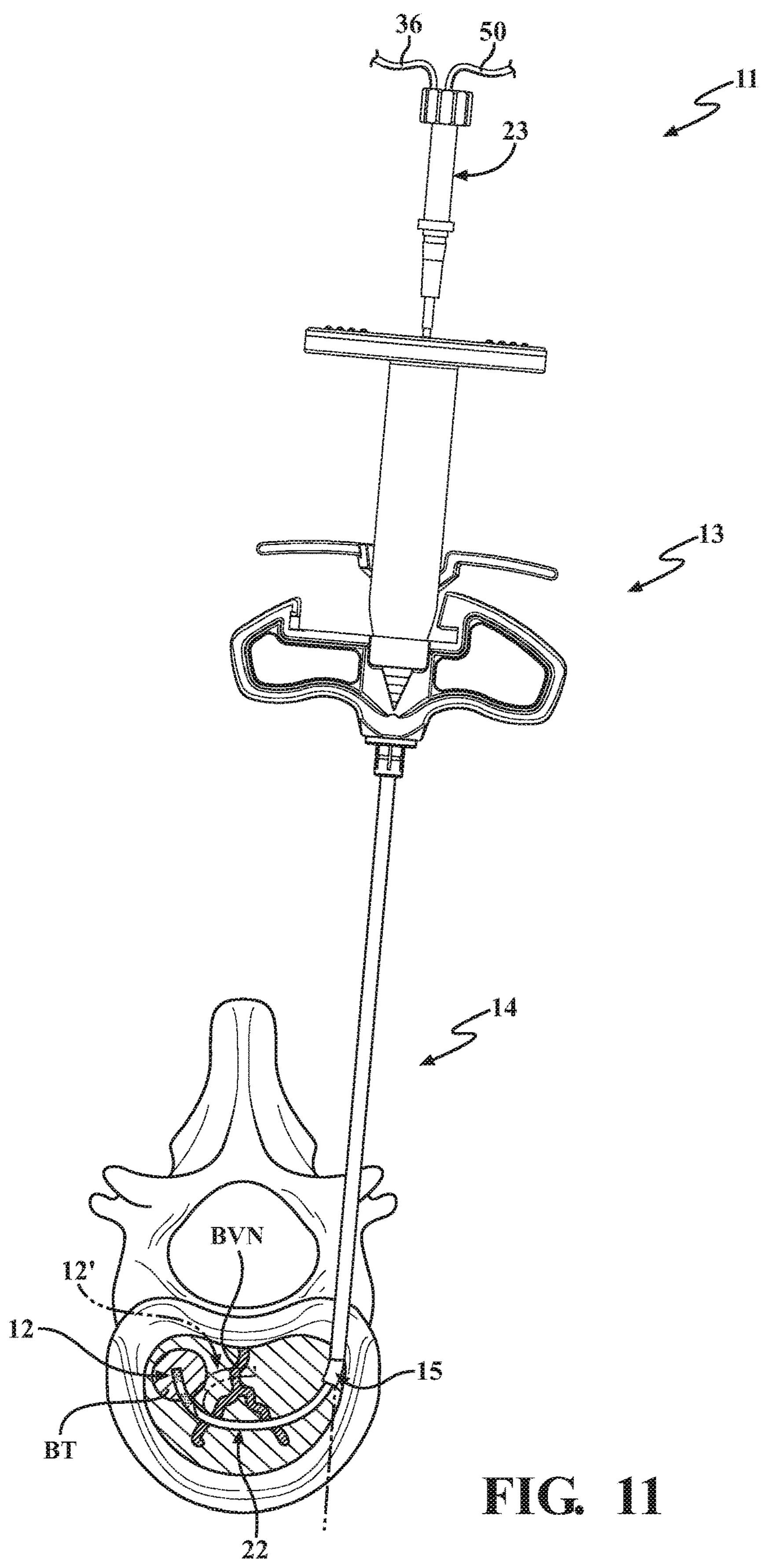
FIG. 11 is a schematic representation of a vertebrae with the electrode assembly being deployed with an introducer assembly to ablate an intraosseous tumor or the basivertebral nerve.

The electrode assembly 12 of the present disclosure facilitates the treatment of tissue in anatomical locations not previously accessible with conventional devices. More particularly, the flexibility of the elongate body 22 provides access to the anatomical locations that require greater degrees of curvature and/or sharper radii of curvature. Referring now to FIG. 11, the elongate body 22 is configured to bend or curve when deployed through the introducer assembly 13. One suitable introducer assembly is disclosed in commonly-owned U.S. Pat. No. 9,839,443, issued Dec. 12, 2017, the entire contents of which are hereby incorporated by reference. In certain implementations, the elongate body 22 has sufficient flexibility to be deployed through a curve of at least 60 degrees, more particularly at least 90 degrees, and even more particularly at least 120 degrees. Further, elongate body 22 has sufficient flexibility to be deployed through the curve having a radius of curvature of within the range of approximately 0.75 to 2.50 inches, more particularly within the range of approximately 1.25 to 2.25 inches.

The ablation system 11 may include the electrode assembly 12, the introducer assembly 13, and an access cannula 14. The ablation system 11 may be packaged as a kit. An exemplary manner by which the ablation system 11 may be deployed is the ablation of a bone tumor (BT) within a vertebral body. The bone tumor is illustrated as markedly posterior and markedly contralateral from the vertebral pedicle through which the access cannula 14 is deployed. The electrode assembly 12 is shown as being deployed through a curve of approximately 180 degrees to access the bone tumor. Another exemplary manner by which the ablation system 11 may be deployed is the ablation of the basivertebral nerve (BVN) within the vertebral body. It is known that for optical results, a main posterior aspect of the basivertebral nerve should be ablated. To access the main posterior aspect of the basivertebral nerve the electrode assembly 12 is shown as deployed through a curve of approximately 270 degrees. Alternatively, the electrode assembly 12 may be deployed through a sharper curve to access the main posterior aspect of the basivertebral nerve.

The access cannula 14 is deployed through the vertebral pedicle, and the introducer assembly 13 may be deployed through the access cannula 14. The introducer assembly 13 may include a sheath 15 configured to be positioned within the vertebral body in a curved configuration beyond the access cannula 14. The electrode assembly 12 is configured to track the curved configuration of the sheath 15 or a curved path within the bone created by the introducer assembly 13. The distal end 20 of the electrode assembly 12 may be approximately positioned in registration with a distal end of the sheath 15. Positioning with the electrode assembly 12 may be confirmed on the x-ray imaging by visualizing the distal cap 46 and the radiopaque marker 106. The sheath 15 may be retracted to expose the proximal and distal emitters 38, 40 of the electrode assembly 12, 12', for example, within the bone tumor or across the basivertebral nerve. The electrode assembly 12, 12' is operated to ablate the bone tumor or the basivertebral nerve. It is appreciated that the ablation system 11 of the present disclosure may be used at any suitable anatomical location, including osseous and non-osseous applications. Exemplary non-osseous applications include facet rhizotomy, sacroiliac nerve block, genicular nerve block, and the like.

The foregoing disclosure is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described. For example, it should be appreciated that inner diameters of the first lumen 34 (and/or the second lumen 35) may not be shown to scale in FIGS. 4-10, but rather exaggerated for meaningful illustration of the components of the electrode assembly 12. In other words, the thermocouple 62, the hypotube 90, and/or the distal lead 92 may be in a relatively form-fitting arrangement within the first lumen 34. Additional medium, for example, a dielectric material, may be provided to occlude any free space in the first lumen 34.

What is claimed is:

1. An electrode assembly comprising:

an elongate body formed from a flexible polymer comprising an outer surface opposite an inner surface defining a lumen and a discharge port in fluid communication with the lumen;

a proximal emitter formed from plating a metal on a first portion of the outer surface;

a distal emitter formed from plating the metal or another metal on a second portion of the outer surface; and a proximal lead extending through the lumen and coupled to the proximal emitter through the discharge port, wherein the first portion and the second portion are spaced apart from one another such that the flexible polymer of the elongate body forms a flexible insulative spacer between the proximal emitter and the distal emitter.

2. The electrode assembly of claim 1, wherein at least one of the proximal emitter and the distal emitter comprises a first layer of copper or nickel adhered to the flexible polymer, and a second layer of gold or platinum plated on the first layer.

3. The electrode assembly of claim 1, further comprising a distal cap coupled to a distal end of the elongate body, wherein the distal cap is formed from conductive material and arranged in electrical communication with the distal emitter.

4. The electrode assembly of claim 3, wherein the electrical communication between the distal cap and the distal emitter is formed from electrodepositing the metal on the distal end of the elongate body.

5. The electrode assembly of claim 3, wherein the distal cap is at least partially secured within the lumen, and wherein the distal emitter is further formed from electrodepositing the metal on the inner surface of the elongate body.

6. The electrode assembly of claim 3, further comprising a distal lead extending through the lumen and in electrical communication with the distal cap.

7. The electrode assembly of claim 3, further comprising:

a thermocouple extending through the lumen and arranged in thermal communication with the distal cap; and a hypotube extending through the lumen and comprising a closed distal end coupled to the distal cap, wherein the thermocouple is disposed within the hypotube.

8. The electrode assembly of claim 7, further comprising a jacket disposed the thermocouple so as to electrically insulate the thermocouple from the hypotube.

9. The electrode assembly of claim 7, wherein the elongate body further defines an infusion port in fluid communication with the lumen to-define a fluid pathway between the inner surface of the elongate body and the hypotube.

10. The electrode assembly of claim 1, further comprising a sheath coaxially disposed over a portion of the proximal emitter, wherein the sheath is formed from non-conductive material such that an exposed portion of the plated metal defines the proximal emitter.

11. The electrode assembly of claim 10, further comprising a proximal lead arranged in electrical communication with the proximal emitter and extending proximally between the sheath and the outer surface of the elongate body.

12. The electrode assembly of claim 11, further comprising a radiopaque marker band securing the proximal lead to the proximal emitter.

13. The electrode assembly of claim 1, wherein the lumen extends longitudinally within a portion of the elongate body and further extends radially outward to the discharge port.

14. An electrode assembly comprising:

an elongate body comprising an outer surface opposite an inner surface defining a first lumen, a second lumen fluidly separated from the first lumen, and a discharge port in fluid communication with the second lumen, wherein the elongate body is formed from non-conductive material;

a proximal emitter formed from plating a metal on a first portion of the outer surface, wherein the plated metal defines a discharge port in fluid communication with the second lumen; and a distal emitter formed from plating the metal or another metal on a second portion of the outer surface, wherein the first portion and the second portion are spaced apart from one another such that the elongate body forms an insulative spacer between the proximal emitter and the distal emitter, wherein the first lumen defines a fluid pathway for fluid received from a fluid source to be discharged through the discharge port, and the second lumen defines an electrical pathway for electrical components of the electrode assembly.

15. The electrode assembly of claim 14, further comprising a proximal lead extending through the first lumen and coupled to the proximal emitter.

16. The electrode assembly of claim 15, wherein the proximal lead is coupled to the proximal emitter through the discharge port.

17. The electrode assembly of claim 14, wherein the electrical components comprise a distal lead extending through the second lumen and coupled to the distal emitter through a hole in the elongate body.

18. The electrode assembly of claim 17, wherein the electrical components comprise a thermocouple extending through the second lumen together with the distal lead.

19. The electrode assembly of claim 14, wherein the first lumen extends longitudinally within a portion of the elongate body and further extends radially outward to the discharge port.

20. An electrode assembly comprising: an elongate body formed from a flexible polymer comprising an outer surface opposite an inner surface defining a lumen and a discharge port in fluid communication with the lumen; a proximal emitter formed from plating a metal on a first portion of the outer surface; a distal emitter formed from plating the metal or another metal on a second portion of the outer surface, wherein the first portion and the second portion are spaced apart from one another such that the flexible polymer of the elongate body forms a flexible insulative spacer between the proximal emitter and the distal emitter; and a proximal lead coupled to the proximal emitter, wherein the lumen extends longitudinally within a portion of the elongate body and further extends radially outward to the discharge port, and wherein the proximal lead is disposed within the lumen.

* * * * *